United States Patent
Kulshrestha et al.

(10) Patent No.: US 10,294,188 B2
(45) Date of Patent: May 21, 2019

(54) PROCESS FOR MAKING ESTERS OF 2-ACETOXYALKANOIC ACIDS USING AN α-HYDROXYALKANOIC ACID ESTER AND AN ACETATE ESTER AS STARTING MATERIALS

(71) Applicant: NatureWorks LLC, Minnetonka, MN (US)

(72) Inventors: Aman Kulshrestha, Plymouth, MI (US); Joseph David Schroeder, Minneapolis, MN (US); Steven Scott Bray, Omaha, NE (US)

(73) Assignee: NatureWorks LLC, Minnetonka, MN (US)

( * ) Notice: Subject to any disclaimer, the term of this patent is extended or adjusted under 35 U.S.C. 154(b) by 0 days.

(21) Appl. No.: 15/120,495

(22) PCT Filed: Feb. 23, 2015

(86) PCT No.: PCT/US2015/017127
§ 371 (c)(1),
(2) Date: Aug. 19, 2016

(87) PCT Pub. No.: WO2015/127372
PCT Pub. Date: Aug. 27, 2015

(65) Prior Publication Data
US 2017/0066709 A1   Mar. 9, 2017

Related U.S. Application Data

(60) Provisional application No. 61/943,989, filed on Feb. 24, 2014.

(51) Int. Cl.
C07C 67/03 (2006.01)
C07C 69/67 (2006.01)
C07C 69/68 (2006.01)

(52) U.S. Cl.
CPC .................................. *C07C 67/03* (2013.01)

(58) Field of Classification Search
None
See application file for complete search history.

(56) References Cited

U.S. PATENT DOCUMENTS

| | | |
|---|---|---|
| 1,927,295 A | 9/1933 | Powers |
| 2,342,613 A | 4/1941 | Hansley |
| 6,992,209 B2 | 1/2006 | Lilga |
| 2012/0078004 A1 | 3/2012 | Fruchey |

FOREIGN PATENT DOCUMENTS

WO   2014/045036 A   3/2014

OTHER PUBLICATIONS

Rehberg, Industrial and Engineering Chemistry vol. 36, #5, pp. 469-472 (1944).
Filchione et al., Industrial and Engineering Chemistry vol. 36, #5, pp. 472-475 (1944).
Rehberg, JACS vol. 67, pp. 56-66 (1945).
Vu et al., Fluid Phase Equilibria 236 (2005) 125-135.

*Primary Examiner* — Amy C Bonaparte

(57) ABSTRACT

2-Acetoxyalkanoic acid esters are made in a reaction of an α-hydroxyalkanoic acid ester and an acetate ester in the presence of a transesterification catalyst. Unlike previous methods for making 2-acetoxyalkanoic acid esters, this process proceeds in high yield and high selectivity to the desired product.

12 Claims, No Drawings

PROCESS FOR MAKING ESTERS OF 2-ACETOXYALKANOIC ACIDS USING AN α-HYDROXYALKANOIC ACID ESTER AND AN ACETATE ESTER AS STARTING MATERIALS

This invention relates to a method for making esters of 2-acetoxyalkanoic acids.

Methyl 2-acetoxypropionate (MAP) is a chemical intermediate of some interest because it can be pyrolyzed to form methyl acrylate and acetic acid. Methyl acrylate is useful as a monomer that can be polymerized to form poly(methylacrylate), and can be converted easily to acrylic acid or other acrylate esters. Therefore, an economical synthetic route to making MAP would have great value.

MAP can be produced in one or more steps starting from lactic acid. Therefore, acrylic acid and acrylate esters can be produced using lactic acid as a starting material. Lactic acid is made in large volumes via fermentation processes and so is both inexpensive and widely available. Acrylic acid and its esters could be produced quite inexpensively if there were an efficient process for converting lactic acid to MAP. However, the known synthetic routes from lactic acid to MAP have been plagued by low conversions and the production of large amounts of unwanted by-products.

Some of the known synthetic routes start with lactic acid itself. For example, lactic acid is known to react with methyl acetate to form MAP, according to the following reaction:

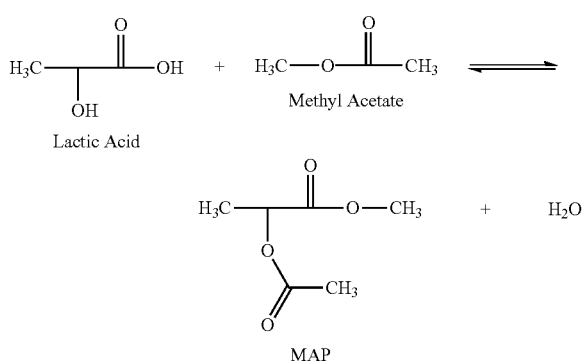

The actual chemistry is much more complicated than this for several reasons. This is an equilibrium reaction, which is reversible and leads to a complicated product mixture. The various products and intermediates interesterify to form unwanted species like methyl lactate and 2-acetoxypropionic acid. Because lactic acid contains both a carboxyl group and a hydroxyl group, it can react with itself to form ester group-containing dimers and oligomers. The product obtained from this reaction, therefore, is a complex mixture of materials. Conversions to MAP are disappointingly low. For example, Rehberg et al., in *Industrial and Engineering Chemistry* Vol. 36, pp. 469-472 (1944) ("Rehberg 1944"), describe conversions to MAP of less than 30%.

In addition, there is always water present in the foregoing process, because water is produced in the reaction. More water is almost always carried into the process with the lactic acid, which is difficult to produce in anhydrous form. The water hydrolyzes the various ester compounds (including the product) back to the starting materials or other acids such as acetic acid. These acids are also corrosive to many metals, so the reaction vessel and associated equipment would need to be made of special alloys. In addition, the water forms an azeotrope with methyl lactate, which is an impurity that forms in large quantities in this reaction. It is difficult and expensive to separate the methyl lactate from the water to recover and recycle the lactic acid values.

Removing water from lactic acid leads to other problems, including the oligomerization of the lactic acid. For this reason, commercially available concentrated lactic acid syrups contain large amounts of oligomers. For example, in a typical commercially available 85% lactic acid syrup, 20% or more of the lactic acid is in the form or dimers or higher oligomers. The presence of these higher oligomers in concentrated lactic acid syrups also leads to diminished yields and unwanted by-products.

Filachione et al., in *Industrial and Engineering Chemistry* Vol. 36 pp. 472-475 (1944) describes an alternative process in which lactic acid is reacted with acetic acid to form 2-acetoxypropionic acid, which is then converted to MAP by reaction with methyl acetate or methanol. In the first step, yields to 2-acetoxypropionic acid are at best 78%. Conversions in the second step are very low. As a result, overall yields to MAP are even lower than those described in Rehberg 1944 (see Filachione et al., page 475).

Other processes start with a lactic acid ester. Alkyl esters of lactic acid react with acetic anhydride, ketene or acetyl chloride to form the corresponding 2-acetoxypropionic acid ester. See, e.g., Rehberg 1944 (cited above) and Rehberg et al., *JACS* vol. 67, pp. 56-56 (1945). These processes provide somewhat better yields, but require special, expensive reagents that can be difficult to regenerate and recycle. U.S. Pat. No. 6,992,209 describes a process in which methyl lactate is reacted with acetic acid to form MAP. In this process, MAP reacts with acetic acid to form 2-acetoxypropionic acid. Because of this, the process forms MAP and 2-acetoxypropionic acid in roughly equal amounts, together with methyl acetate, and so is a low-yield process.

There is a need in the art to provide an inexpensive route to MAP and other esters of 2-acetoxypropionic acid.

This invention is a process for making a 2-acetoxyalkanonic acid ester. The process comprises heating a mixture of an alkyl or aryl ester of an α-hydroxyalkanoic acid and at least one mole of an alkyl or aryl acetate per mole of the α-hydroxyalkanoic acid ester to a temperature of at least 150° C. under superatmospheric pressure in the presence of a transesterification catalyst to convert at least a portion of the α-hydroxyalkanoic acid ester and acetate ester to a 2-acetoxyalkanoic acid ester and at least one alkanol or phenolic compound.

This process differs from the prior art methods in part in that both the lactic starting material and the acetate starting material are provided in the form of esters.

This process surprisingly produces 2-acetoxyalkanoic acid esters in high yields from these inexpensive starting materials. Because the starting materials (apart from the catalysts, which are used in small quantities) are not acids and can be provided in substantially anhydrous form, and few acid species are formed during the reaction, there is little corrosion of metallic reaction vessels. The main reaction by-product is an alkanol or phenolic compound, which is easily recovered and recycled (if desired) to form more of the starting materials.

The ester of the α-hydroxyalkanoic acid is an ester corresponding to the reaction product of α-hydroxyalkanoic acid and an alkanol or phenolic compound (although it can be prepared by various methods, the method of preparation being unimportant to this invention). The ester of the α-hydroxyalkanoic acid in some embodiments is represented by the structure:

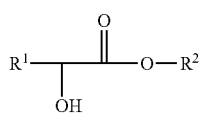

wherein R¹ is hydrogen or alkyl (including linear, branched and cycloalkyl) and R² is alkyl (including linear, branched and cycloalkyl) or aryl. R¹ and/or R² may have substituents that are inert (i.e., do not react) under the conditions of the process. Examples of such substituents include, for example, halogen, aryl (if R² is alkyl), alkyl (if R² is aryl), ether and the like.

R¹ is in some embodiments an unsubstituted alkyl group. It preferably contains up to six carbon atoms. R¹ may be methyl, ethyl, n-propyl, i-propyl, n-butyl, sec-butyl, t-butyl, cyclohexyl, and the like. R¹ is preferably methyl, in which case the ester is a lactate ester. When R¹ is other than hydrogen, the carbon atom alpha to the carbonyl carbon will be chiral. Either the R- or S-enantiomer, or a mixture thereof, is useful.

R² is preferably an unsubstituted alkyl group containing up to six carbon atoms, or phenyl. When alkyl, R² may be methyl, ethyl, n-propyl, i-propyl, n-butyl, sec-butyl, t-butyl, cyclohexyl, and the like. R² is preferably methyl, n-butyl or phenyl.

The acetate ester corresponds to an ester of acetic acid with an alkanol or or a phenolic compound (although it can be made using various methods). The alkyl acetate corresponds to the structure:

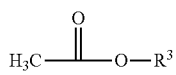

wherein R³ is defined in the same way as R² above. R³ is preferably an unsubstituted alkyl group containing up to six carbon atoms, or phenyl. If alkyl, R³ may be methyl, ethyl, n-propyl, i-propyl, n-butyl, sec-butyl, t-butyl, cyclohexyl, aryl, and the like. R³ is preferably methyl, n-butyl or phenyl. Methyl is especially preferred, especially when producing MAP, because the resulting alcohol by-product (methanol) is volatile and easily removed from the product, and, when the MAP is subsequently used as a raw material for manufacturing methyl acrylate, the lack of β-hydrogens limits unwanted side reactions during the pyrolysis reaction.

The alkyl or aryl group of the acetate ester and the alkyl or aryl group of the α-hydroxyalkanoic acid ester are preferably the same, i.e., for any reaction, R² preferably is the same as R³. The acetate ester is most preferably methyl acetate and the α-hydroxyalkanoic acid ester is most preferably the methyl ester. The α-hydroxyalkanoic acid ester is most preferably methyl lactate.

The idealized reaction of the acetate ester and the α-hydroxyalkanoic acid ester is as follows:

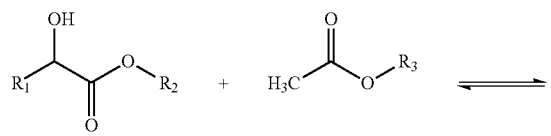

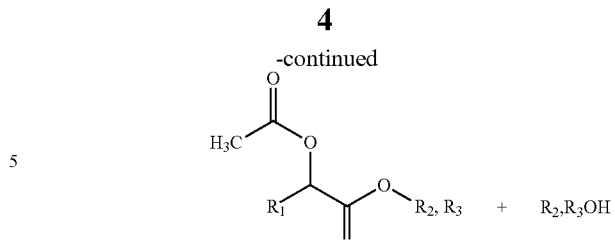

where R¹, R² and R³ are as before. The notation "R²,R³" denotes that the indicated molecule will be a mixture of species having an R² group and species having an R³ group (in cases where R² and R³ are different). Thus, for example, the R²,R³OH by-product will be a mixture of alkanets and/or phenolic compounds when R² and R³ are different, and will be a single alkanol or phenolic compound when R² and R³ are the same (as preferred). Similarly, the 2-acetoxyalkanoate ester product will be a mixture of esters if R² and R³ are different, and will be a single ester when R² and R³ are the same. Most preferably, R² and R³ are both methyl, the alkanol by-product is methanol, and the 2-acetoxyalkanoate ester product is the methyl ester.

To perform the reaction, the acetate ester is combined with the α-hydroxyalkanoic acid ester at a mole ratio of at least 1:1. It is preferred to combine the α-hydroxyalkanoic acid ester with an excess of the acetate ester, as this helps to drive the equilibrium toward the desired product. A preferred molar ratio of acetate ester to α-hydroxyalkanoic acid ester is at least 2:1, at least 5:1, at least 10:1 or at least 20:1, and the mole ratio may be 100:1 or even higher.

The transesterification catalyst is a material that catalyzes ester exchange reactions. Suitable transesterification catalysts are well known in the art. Among these are strong Bronsted acids such as alkyl or aryl sulfonic acid compounds like para-toluenesulfonic acid, hydrochloric acid, sulfuric acid, phosphoric acid or oligomers of phosphoric acid. Strong Lewis acids are also suitable. These include, for example, tin chloride, tin oxide, dialkyl tin oxides, alkyltinalkoxides, alkyltincarboxylates, various titanium or aluminum compounds, boron trifluoride and the like.

The catalyst is used in catalytic quantities, which are typically 0.001 to 0.25 mole of the catalyst per mole of the α-hydroxyalkanoic acid ester.

It is not necessary to perform the reaction in a solvent or diluent, although one can be provided if desired. The solvent or diluent should not react under the conditions of the process. Examples of suitable solvents or diluents include hydrocarbons, ketones, chlorinated hydrocarbons, ethers, polyethers, and the like.

Water should be present in at most very small quantities, as water can engage in various reactions with the starting materials and reaction products to form acids and other unwanted species. It is preferred to provide the acetate ester and α-hydroxyalkanoic acid ester in substantially anhydrous form, i.e., each containing less than 1% by weight water and each preferably containing less than 0.8% or less than 0.5% by weight water. Other sources of water preferably are excluded. Any atmosphere under which the reaction is performed preferably is substantially anhydrous. Overall, it is preferred that that water content in the reaction vessel during the reaction is maintained at below 1% by weight, more preferably below 0.5% by weight, and still more preferably below 0.15% by weight.

The reaction is performed at a temperature of at least 150° C. under superatmospheric pressure. A preferred temperature is at least 175° C., and a still more preferred temperature is at least 190° C. A suitable maximum temperature is 230° C., as higher temperatures are disadvantageous because lactic acid begins to decompose at those higher temperatures.

The aforementioned temperatures are greater than the boiling points of the starting materials. Therefore, the reaction is performed at superatmospheric pressure sufficient to maintain the starting materials as liquids during the reaction. A pressure of 10 to 60 atmospheres (1010 to 6060 kPa) is generally suitable, and a preferred pressure is 20 to 50 atmospheres (2020 to 5050 kPa).

The reaction can be performed continuously, semicontinuously or batch-wise in equipment capable of withstanding the operating temperature and pressure. Equipment that comes into contact with the hot reaction mixture and/or hot product mixture is preferably resistant to acids. Batch-type reactors include Parr reactors and other pressurized vessels. Continuous and semi-continuous reactors include pipe or tube reactors, loop reactors, continuously stirred tank reactors, and the like.

The reaction is continued until at least a portion of the starting materials is converted to the desired 2-acetoxypropionic acid ester. The reaction is an equilibrium reaction. Therefore, unless one or more of the products is removed as the reaction proceeds, the reaction mixture will reach an equilibrium prior to full conversion of the limiting starting material (typically, the α-hydroxyalkanoic acid ester) to product. Without removal of reaction products, the conversion of the limiting starting material will typically reach 50 to 80% if the reaction conditions are maintained for enough time. Higher conversions can be obtained if one or more reaction products (such as the alkanol or phenolic compound) are removed or when the acetate ester is used in larger excess.

In a batch process, a typical reaction time is 15 minutes to 10 hours. It is preferable to minimize reaction times to reduce the formation of unwanted by-products; in a preferred process, the reaction is discontinued when the conversion of the limiting starting material reaches 40 to 90%, especially 40 to 80%, or when the reaction mixture reaches equilibrium.

A benefit of the inventive process is it is highly selective to the desired 2-acetoxyalkanonic acid ester. Selectivities of at least 80% or even 90% or higher to the desired product can be obtained easily with this invention. Selectivity is calculated by (a) determining the amount of starting α-hydroxyalkanoic acid ester consumed, (b) calculating the amount (B) of 2-acetoxyalkanonic acid ester that would have been produced if all the consumed α-hydroxyalkanoic acid ester had been converted to 2-acetoxyalkanonic acid ester, (c) determining the amount (C) of 2-acetoxyalkanonic acid ester produced, and (d) dividing C by B and multiplying by 100%. The main by-products of the reaction are an alkanol or phenolic compound and a small amount of oligomers of the α-hydroxyalkanoic acid, which may be in the form of esters.

Yields to the desired 2-acetoxyalkanonic acid ester are often at least 40%, based on the starting α-hydroxyalkanoic acid ester, and are often 50 to 75% or higher. Yields are calculated as the amount of 2-acetoxyalkanoic acid ester produced divided by the amount that would be produced if all of the starting α-hydroxyalkanoic acid ester were converted to 2-acetoxyalkanoic acid ester.

The desired 2-acetoxyalkanonic acid ester is easily separated from the remaining components of the crude product mixture using distillation, crystallization, solvent extraction or other methods. Volatile components of the reaction mixture, such as the alkanol or phenolic compound, are easily flashed or otherwise distilled off. The 2-acetoxyalkanonic acid ester in most cases has a higher boiling temperature and a higher melting temperature than the starting materials. These differences in boiling and melting temperatures can be exploited as the basis for distillation and/or crystallization recovery processes.

Unreacted starting materials may be recovered, purified if necessary and recycled into the process. The alkanol or phenolic compound formed in the process can be recovered, purified if necessary, and then reacted with an α-hydroxyalkanoic acid and/or acetic acid to regenerate either or both of the starting reagents. Oligomers of the α-hydroxyalkanoic acid (or esters of such oligomers) can be hydrolyzed back to the corresponding α-hydroxyalkanoic acid (or ester thereof), and recycled into the process.

The process of the invention is particularly useful for forming 2-acetoxypropionic acid esters by reaction of a lactate ester (preferably methyl lactate) with an acetate ester (preferably methyl acetate). The 2-acetoxypropionic acid ester product can by pyrolized to form acetic acid and an acrylate ester in which the ester group corresponds to the $R^2$ and/or $R^3$ group in the starting materials. Pyrolysis can be performed by heating the 2-acetoxypropionic acid ester to a temperature of 400 to 600° C. under a non-oxidizing atmosphere. The acrylate ester is a useful monomer that can be polymerized or copolymerized to form acrylate polymers and copolymers. The acrylate ester can be hydrolyzed to form acrylic acid, which is itself a useful monomer, or can be converted to other acrylate monomers. The acetic acid can reacted with an alkanol or phenolic compound to regenerate the starting acetic ester, which can be recycled back into the process of this invention.

The process of the invention is also useful for producing butylacetoxypropionic acid. Butylacetoxypropionic acid is a useful starting material for an enzyme-catalyzed stereoselective deacylation process as described, for example, in WO 2014/045036.

The following examples are provided to illustrate the invention, and are not intended to limit the scope thereof. All parts and percentages are by weight unless otherwise indicated.

EXAMPLES 1-2

Example 1

1 mole of methyl lactate (water content about 0.04 weight percent), 25 moles of methyl acetate (water content about 0.5 weight percent) and 0.05 mole of p-toluenesulfonic acid are charged to a Parr reactor. The reactor is pressurized to 90 pounds/square inch (about 620 kPa) with nitrogen to test for leaks, and then vented back to atmospheric pressure. The reactor and its contents are heated to 200° C. for 3 hours, during which time a pressure of 400 pounds/square inch (about 2750 kPa) develops in the reactor. The reaction mixture is then cooled to room temperature in the closed reactor. The reactor contents are removed and analyzed for residual methyl lactate, the desired product (methyl 2-acetoxypropionic acid (MAP)), and lactic acid oligomers (including alkyl esters thereof) by gas chromatography with a flame ionization detector using commercially available standards. Conversion of methyl lactate is calculated from the amount of methyl lactate remaining in the reaction mixture. Selectivity to MAP is calculated from the measured amounts of MAP and oligomers. Yield to MAP is calculated as conversion multiplied by selectivity. Results are as indicated in Table 1.

Example 2 is performed in the same manner, except the p-toluenesulfonic acid is replaced with an equivalent amount of tin chloride dihydrate. Results are indicated in Table 1.

TABLE 1

| Designation | Catalyst | Conversion of Methyl Lactate | Selectivity to MAP | Overall Yield to MAP (based on methyl lactate) |
|---|---|---|---|---|
| Ex. 1 | p-TSA[1] | 60% | 89% | 53.4% |
| Ex. 2 | SnCl$_2$[1] | 74% | 93% | 68.8% |

[1]p-TSA is para-toluenesulfonic acid. SnCl$_2$ is tin chloride dihydrate.

The conversion, selectivity and overall yield to MAP are extremely high in relation to prior art processes. In these experiments, the tin catalyst promotes a faster reaction rate as indicated by the higher methyl lactate conversion. A higher conversion is achieved for Example 1 when the reaction is continued for a longer time.

Example 3

1 mole of n-butyl lactate (water content less than 0.1 weight-%), 25 moles of n-butyl acetate (water content about 0.5 weight-% or less) and 0.05 mole of tin chloride dihydrate are charged to a Parr reactor. The reactor is pressurized to 90 pounds/square inch (about 620 kPa) with nitrogen to test for leaks, and then vented back to atmospheric pressure. The reactor and its contents are heated to 200° C. for 3 hours, during which time a pressure of 100 pounds/square inch (about 690 kPa) develops in the reactor. The reaction mixture is then cooled to room temperature in the closed reactor. The reactor contents are removed and analyzed for residual butyl lactate, the desired product (butyl-2-acetoxypropionic acid (BAP)), and lactic acid oligomers (including alkyl esters thereof) by gas chromatography with a flame ionization detector using commercially available standards. Conversion of butyl lactate is calculated from the amount of butyl lactate remaining in the reaction mixture. Selectivity to BAP is calculated from the measured amounts of BAP and oligomers. Yield to BAP is calculated as conversion multiplied by selectivity. Results are as indicated in Table 2.

TABLE 2

| Designation | Catalyst | Conversion of Butyl Lactate | Selectivity to BAP | Overall Yield to BAP (based on butyl lactate) |
|---|---|---|---|---|
| Ex. 3 | SnCl$_2$[1] | 64% | 93% | 60% |

[1]SnCl$_2$ is tin chloride dihydrate.

This experiment demonstrates that the similarly high conversions, selectivities and overall yields to desired product are obtained when producing BAP instead of MAP.

What is claimed is:

1. A process for making a 2-acetoxyalkanoic acid ester comprising heating a mixture of an α-hydroxyalkanoic acid ester and at least one mole of an alkyl acetate ester per mole of the α-hydroxyalkanoic acid ester in a reaction vessel to a temperature of at least 150° C. under superatmospheric pressure in the presence of a transesterification catalyst to convert at least a portion of the α-hydroxyalkanoic acid ester and alkyl acetate ester to a 2-acetoxyalkanoic acid ester and at least one alkanol or phenolic compound, wherein a water content in the reaction vessel during the reaction is maintained at below 0.15% by weight, the process being characterized by a selectivity of at least 80% to the 2-acetoxyalkanonic acid ester and a yield of 2-acetoxyalkanoic acid ester is 50 to 75%, based on the starting amount of the α-hydroxyalkanoic acid ester.

2. The process of claim 1, wherein the ester of the α-hydroxyalkanoic acid is represented by the structure:

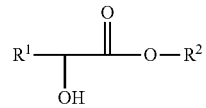

wherein R$^1$ is hydrogen, linear alkyl, branched alkyl or cycloalkyl and R$^2$ is linear alkyl or branched alkyl.

3. The process of claim 2, wherein the acetate ester is represented by the structure:

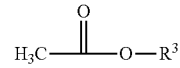

wherein R$^3$ is linear alkyl or branched alkyl.

4. The process of claim 3, wherein R$^2$ and R$^3$ each are independently methyl, ethyl, n-propyl, i-propyl, n-butyl, sec-butyl or t-butyl and R$^1$ is methyl, ethyl, n-propyl, i-propyl, n-butyl, sec-butyl or t-butyl.

5. The process of claim 4, wherein R$^2$ and R$^3$ are the same.

6. The process of claim 5, wherein R$^2$ and R$^3$ each are methyl.

7. The process of claim 5, wherein R$^2$ and R$^3$ each are n-butyl.

8. The process of claim 5, wherein R$^1$ is methyl.

9. The process of claim 1, further comprising recovering the 2-acetoxyalkanoic acid ester.

10. The process of claim 9, wherein the 2-acetoxyalkanoic acid ester is recovered by crystallization or distillation.

11. The process of claim 1, wherein the conversion of the α-hydroxyalkanoic acid ester is 50 to 80%.

12. The process of claim 1, wherein the selectivity to the 2-acetoxyalkanoic acid ester is at least 90%.

* * * * *